US012743775B2

(12) United States Patent
Aggarwal et al.

(10) Patent No.: US 12,743,775 B2
(45) Date of Patent: Sep. 22, 2026

(54) BIOMARKERS OF COLLAGEN FIBER ARCHITECTURE IN EPITHELIAL OVARIAN CANCER (EOC) PATIENTS

(71) Applicant: Case Western Reserve University, Cleveland, OH (US)

(72) Inventors: Arpit Aggarwal, Cleveland, OH (US); Haojia Li, Cleveland Heights, OH (US); Anant Madabhushi, Decatur, GA (US)

(73) Assignee: Case Western Reserve University, Cleveland, OH (US)

( * ) Notice: Subject to any disclaimer, the term of this patent is extended or adjusted under 35 U.S.C. 154(b) by 331 days.

(21) Appl. No.: 18/490,205

(22) Filed: Oct. 19, 2023

(65) Prior Publication Data

US 2025/0037272 A1 Jan. 30, 2025

Related U.S. Application Data

(60) Provisional application No. 63/516,153, filed on Jul. 28, 2023.

(51) Int. Cl.

| | |
|---|---|
| ***G06K 9/00*** | (2022.01) |
| ***G06T 7/00*** | (2017.01) |
| ***G16H 50/20*** | (2018.01) |

(52) U.S. Cl.
CPC .......... *G06T 7/0012* (2013.01); *G16H 50/20* (2018.01); *G01N 2800/52* (2013.01); *G06T 2207/20081* (2013.01); *G06T 2207/30024* (2013.01)

(58) Field of Classification Search
None
See application file for complete search history.

(56) References Cited

U.S. PATENT DOCUMENTS

2020/0242756 A1* 7/2020 Madabhushi ............. G06T 7/45
2021/0169336 A1* 6/2021 Sanchez ............... A61B 5/7264

* cited by examiner

*Primary Examiner* — Wei Wen Yang
(74) *Attorney, Agent, or Firm* — Eschweiler & Potashnik, LLC

(57) ABSTRACT

The present disclosure, in some embodiments, relates to a method for determining a prognosis. The method includes measuring a collagen fiber orientation disorder (CFOD) within a digitized pathology image of a pathology slide corresponding to a patient that has or that has had EOC. A plurality of CFOD features are generated using the measured CFOD. A machine learning model is operated upon the plurality of CFOD features to determine an EOC prognosis for the patient.

20 Claims, 10 Drawing Sheets

| Feature Index | Feature description | HR (per unit increase) |
|---|---|---|
| 1 | Mean entropy value of a collagen fiber orientation disorder feature map using a 200 x 200 pixel neighborhood | 0.75 |
| 2 | Minimum entropy value of a collagen fiber orientation disorder feature map using a 200 x 200 pixel neighborhood | 0.5 |
| 3 | Maximum entropy value of a collagen fiber orientation disorder feature map using a 250 x 250 pixel neighborhood | 0.94 |
| 4 | Minimum entropy value of a collagen fiber orientation disorder feature map using a 350 x 350 pixel neighborhood | 0.84 |
| 5 | Minimum entropy value of a collagen fiber orientation disorder feature map using a 400 x 400 pixel neighborhood | 0.64 |
| 6 | Minimum entropy value of a collagen fiber orientation disorder feature map using a 450 x 450 pixel neighborhood | 1.64 |
| 7 | Maximum entropy value of a collagen fiber orientation disorder feature map using a 550 x 550 pixel neighborhood | 1.38 |
| 8 | Maximum entropy value of a collagen fiber orientation disorder feature map using a 600 x 600 pixel neighborhood | 0.36 |

| | p-value | Hazard Ratio (95% Confidence Interval) |
|---|---|---|
| Age (<60) | 0.06 | 2.08 (0.96-4.5) |
| Stage (FIGO II, III, IV) | 0.04 | 2.3 (1.02-5.2) |
| CFOD (Low vs High) | 0.03 | 2.47 (1.07-5.7) |

BIOMARKERS OF COLLAGEN FIBER ARCHITECTURE IN EPITHELIAL OVARIAN CANCER (EOC) PATIENTS

REFERENCE TO RELATED APPLICATION

This Application claims the benefit of U.S. Provisional Application No. 63/516,153, filed on Jul. 28, 2023, the contents of which are hereby incorporated by reference in their entirety.

FEDERAL FUNDING NOTICE

This invention was made with government support under CA199274 and CA249992 awarded by the National Institutes of Health. The government has certain rights in the invention. This work was supported by the U.S. Department of Veterans Affairs, and the Federal Government has certain rights in this invention.

BACKGROUND

Ovarian cancer begins when cells in or near the ovaries develop changes (mutations) in their DNA. The changes in the cell's DNA result in the growth of cancerous cells within tissue of the ovaries, fallopian tubes, and/or peritoneum. As ovarian cancer progresses, the cancerous cells may eventually form a tumor. Ultimately, the cancerous cells will spread into the surrounding tissues.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIGS. 3A-3C illustrate some exemplary images corresponding to a measurement of CFOD features within a whole slide image (WSI).

FIG. 4 illustrates a table showing some exemplary CFOD features that have been found to be determinative of an EOC survival prognosis (e.g., 5-year overall survival) for a patient.

DETAILED DESCRIPTION

Figure 1:
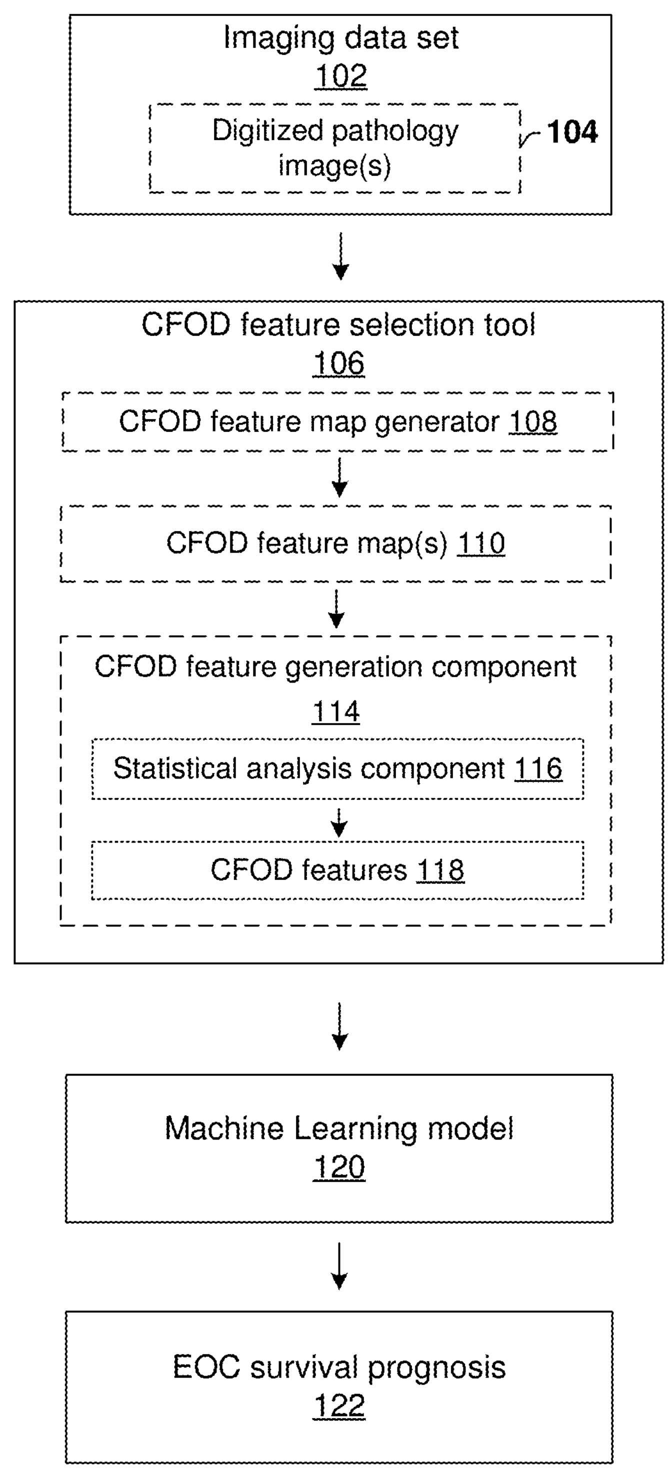
FIG. 1 illustrates a block diagram of some embodiments of an epithelial ovarian cancer (EOC) assessment system that is configured to determine a prognosis for a patient using collagen fiber orientation disorder (CFOD) features extracted from one or more digitized pathology images of EOC tissue of the patient.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

Ovarian cancer causes more deaths per year than any other form of cancer within the female reproductive system. There are different types of ovarian cancer. The most common type of ovarian cancer is epithelial ovarian cancer. Epithelial ovarian cancer is a cancer that develops in epithelial tissue contained within a thin lining that covers the ovaries. Epithelial ovarian cancer accounts for approximately 90% to approximately 95% of ovarian cancers, and has a five-year overall survival of less than 50%.

Early detection of epithelial ovarian cancer is difficult as epithelial ovarian cancer rarely causes symptoms in its early stages. By the time symptoms occur, epithelial ovarian cancer may be a higher stage and difficult to treat. Most commonly, epithelial ovarian cancer may be treated by surgically removing as much of a tumor as possible (e.g., with debulking surgery). Following the surgery, a patient may be subsequently treated with adjuvant chemotherapy to try to avoid recurrence of the cancer. However, while most patients are initially cured, epithelial ovarian cancer will eventually return in the majority of patients. Because of the relatively high rate of recurrence with epithelial ovarian cancer, along with the relatively low five-year overall survival, there is a need for improved prognostic tools to assess the long term survival (e.g., the 5-year overall survival) of patients that have been treated for epithelial ovarian cancer.

The epithelial tissue covering the ovaries contains collagen fibers. It has been appreciated that collagen fiber organization may be associated with epithelial ovarian cancer prognosis. It has been also appreciated that computational and machine learning tools may be used to develop a quantitative biomarker of collagen fiber orientation disorder (CFOD) from digitized pathology images (e.g., of Hematoxylin and Eosin stained slides) of epithelial ovarian cancer tissue. The quantitative biomarker of CFOD may be associated with an overall survival in women undergoing surgical resection followed by adjuvant chemotherapy, thereby providing health care providers with a valuable tool in assessing the long term survival of patients that have been treated for epithelial ovarian cancer.

In some embodiments, the present disclosure relates to a method and associated apparatus for determining an epithelial ovarian cancer (EOC) survival prognosis for a patient using collagen fiber orientation disorder (CFOD) features extracted from digitized pathology images of EOC tissue excised from the patient. The method may be performed by partitioning a digitized pathology image corresponding to an EOC patient into a plurality of neighborhoods. A CFOD value is determined for each of the plurality of neighborhoods. A CFOD feature map is then generated for the digitized pathology image using the CFOD values for the plurality of neighborhoods. A statistical analysis of the CFOD feature map is performed to form a plurality of statistical CFOD features. A plurality of CFOD features are selected from the plurality of statistical CFOD features. A machine learning model is operated upon the plurality of CFOD features to determine a risk of death for the patient from the EOC. By operating a machine learning model on digitized pathology images of a patient to determine an EOC survival prognosis, the disclosed method is able to provide potential insight on patients that have been treated for EOC. The potential insight can offer medical professionals support in management of EOC patients.

FIG. 1 illustrates a block diagram of some embodiments of an EOC assessment system 100 that is configured to determine a prognosis for a patient using collagen fiber orientation disorder (CFOD) features extracted from one or more digitized pathology images of EOC tissue of the patient.

The EOC assessment system 100 comprises an imaging data set 102. The imaging data set 102 includes imaging data for a patient that has or that has had epithelial ovarian cancer (EOC). In some embodiments, the imaging data set 102 comprises one or more digitized pathology images 104 (e.g., one or more digitized biopsy slides) obtained from a pathological tissue sample taken from the patient and stored in an electronic memory. In some embodiments, the tissue sample may be taken from the patient as part of a surgical resection (e.g., a debulking surgery).

A CFOD feature selection tool 106 is configured to extract a plurality of CFOD features 118 from the one or more digitized pathology images 104. The plurality of CFOD features 118 quantify disorder in collagen fiber orientations within the or more digitized pathology images 104. In some embodiments, the CFOD feature selection tool 106 may be configured to measure (e.g., calculate) a collagen fiber orientation disorder (CFOD) associated with the one or more digitized pathology images 104, and to generate the plurality of CFOD features 118 from the measured CFOD. In some embodiments, the CFOD may be measured by quantifying entropy of collagen fiber orientations in the one or more digitized pathology images 104. For example, the CFOD may be measured by quantifying entropy of collagen fiber orientations in stromal regions and/or epithelial regions of the one or more digitized pathology images 104. The measurement of CFOD through quantifying entropy is possible as it has been appreciated that entropy represents a level of uncertainty in the orientation of collagen fibers.

In some embodiments, the CFOD feature selection tool 106 may comprise a CFOD feature map generator 108 and a CFOD feature generation component 114. The CFOD feature map generator 108 is configured to generate one or more CFOD feature maps 110 respectively showing CFOD values at different locations over the one or more digitized pathology images 104. The CFOD feature generation component 114 is configured to generate the plurality of CFOD features 118 from the one or more CFOD feature maps 110. In some embodiments, the plurality of CFOD features 118 comprise statistical measures (e.g., first order statistics) of the CFOD values within the one or more CFOD feature maps 110.

The plurality of CFOD features 118 are provided to a machine learning model 120 that is configured to utilize the plurality of CFOD features 118 to generate an EOC survival prognosis 122 (i.e., an EOC survival prediction) for the patient. In some embodiments, the EOC survival prognosis 122 may comprise a number denoting a risk of death. For example, the risk of death may include a numerical value that is indicative of an overall survival (e.g., a 5-year overall survival) associated with the patient. In some embodiments, the machine learning model 120 is configured to determine an EOC survival prognosis 122 that is an overall survival of the patient as being inversely proportional to a measured CFOD of a digitized pathology image of the patient. For example, the machine learning model 120 will determine a higher likelihood of overall survival for a patient having a low measured CFOD, while a patient having a high measured CFOD will have a lower likelihood of overall survival.

Therefore, by using the plurality of CFOD features 118 extracted from the one or more digitized pathology images 104, the disclosed EOC assessment system 100 may be able to generate an EOC survival prognosis 122 that provides an accurate prediction of a patient's overall survival after treatment for EOC (e.g., after surgical resection and/or adjuvant chemotherapy). The prediction of overall survival can be taken into consideration by a health care professional when determining how to manage care of the patient. By having a more accurate idea of a patient's likelihood of recurrence and/or death, the health care profession and/or patient are able to make more informed decisions regarding care of the patient. For example, an EOC survival prognosis 122 indicating better overall survival may indicate that a patient should receive aggressive adjuvant chemotherapy, while an EOC survival prognosis 122 indicating better overall survival may indicate that a patient should receive less aggressive adjuvant chemotherapy.

Figure 2:
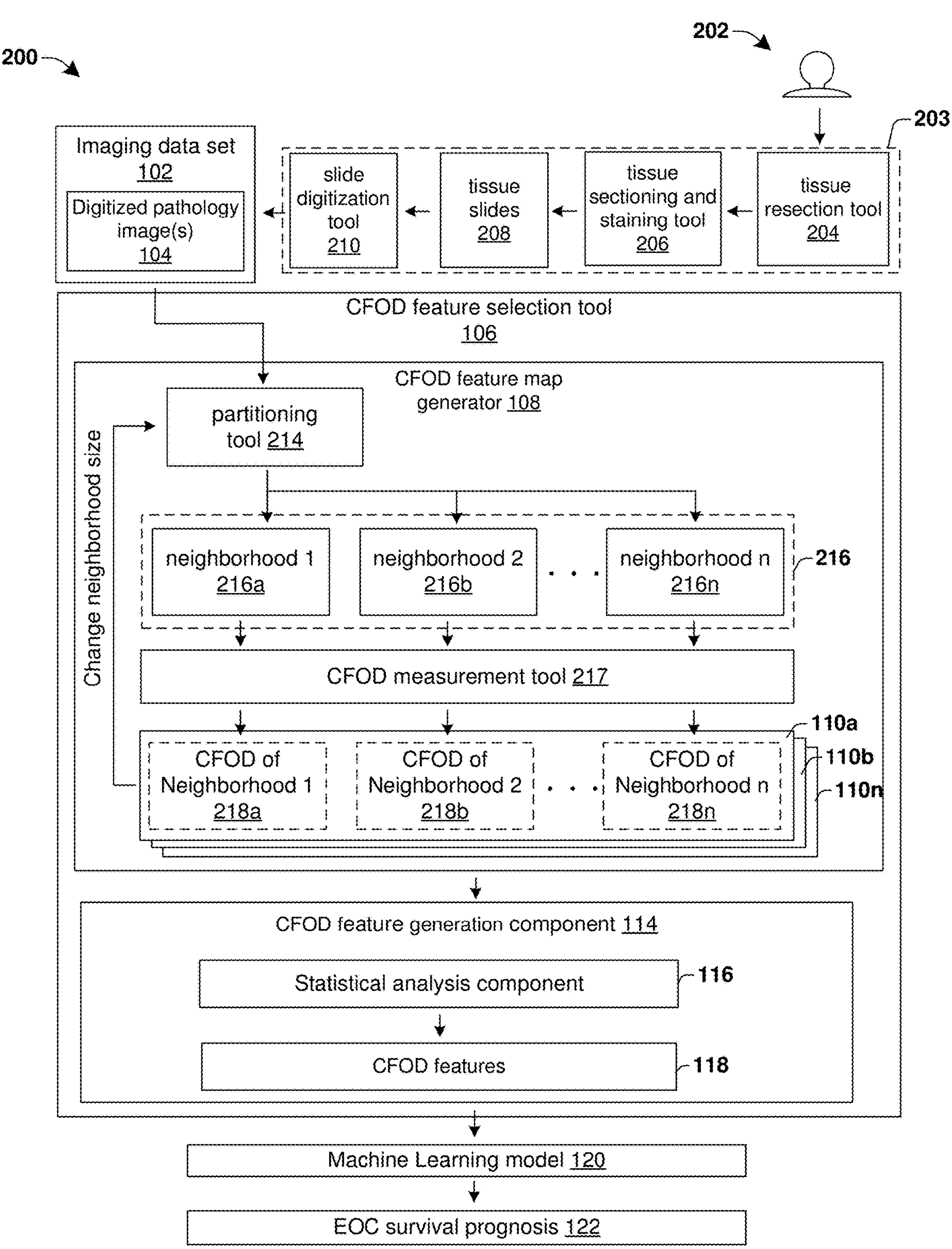
FIG. 2 illustrates a block diagram of some additional embodiments of an EOC assessment system that is configured to determine a prognosis for a patient using CFOD features extracted from one or more digitized pathology images of EOC tissue of the patient.

FIG. 2 illustrates a block diagram of some additional embodiments of an EOC assessment system 200 that is configured to determine a prognosis for a patient using CFOD features extracted from one or more digitized pathology images of EOC tissue of the patient.

The EOC assessment system 200 comprises an imaging data set 102 including imaging data for a patient 202. In some embodiments, the imaging data set 102 comprises one or more digitized pathology images 104 obtained from a pathological tissue sample taken from the patient 202. In some embodiments, the patient 202 may be a treatment naive patient (e.g., a patient that has not received treatment by chemotherapy, radiation, and/or the like). The one or more digitized pathology images 104 may comprise whole slide images (WSIs) of epithelial tissue including EOC (e.g., including an EOC tumor).

In some embodiments, the one or more digitized pathology images 104 may be generated by a slide generation stage 203 that is configured to digitize a stained slide generated from a tissue sample taken from the patient 202. In some embodiments, the slide generation stage 203 may comprise a tissue resection tool 204 (e.g., a scalpel, a needle, scissors, and/or the like) that is used to surgically excise tissue from the patient 202. The tissue contains epithelial tissue including EOC. The tissue is provided to a tissue sectioning and staining tool 206, which is configured to slice the tissue into thin slices that are placed on one or more transparent slides (e.g., one or more glass slides). The tissue on the one or more transparent slides is then stained to generate one or more tissue slides 208. The one or more tissue slides 208 are subsequently converted to the one or more digitized pathology images 104 by a slide digitization tool 210 (e.g., comprising an CMOS image sensor, a CCD camera, and/or the like). The one or more digitized pathology images 104 are stored within the imaging data set 102. In some embodiments, the one or more digitized pathology images 104 may comprise a whole slide image of a H&E (Hematoxylin and Eosin) stained slide.

A CFOD feature selection tool 106 is configured to access the one or more digitized pathology images 104 and to extract a plurality of CFOD features 118 from the one or more digitized pathology images 104. In some embodiments, the CFOD feature selection tool 106 may comprise a CFOD feature map generator 108 and a CFOD feature generation component 114. In some embodiments, the CFOD feature map generator 108 and the CFOD feature generation component 114 may be implemented as computer code run by a processing unit (e.g., a central processing unit including one or more transistor devices configured to operate computer code to achieve a result, a microcontroller, or the like).

The CFOD feature map generator 108 comprises a partitioning tool 214 that is configured to partition respective ones of the one or more digitized pathology images 104 into a plurality of neighborhoods 216*a*-216*n* (e.g., tumor neighborhoods). In some embodiments, the partitioning tool 214 may partition tumor regions within respective ones of the one or more digitized pathology images 104 into a plurality of neighborhoods 216*a*-216*n*, while not partitioning non-tumor regions. In some such embodiments, the tumor regions may be identified within the one or more digitized pathology images 104 using a deep learning segmentation tool that operates a deep learning segmentation algorithm on the one or more digitized pathology images 104 prior to partitioning.

In some embodiments, the partitioning tool 214 may partition the one or more digitized pathology images 104 into a plurality of neighborhoods 216*a*-216*n* having different sizes during different iterations. For example, during a first iteration the partitioning tool 214 may partition a digitized pathology image into a first plurality of neighborhoods having a first size, during a second iteration the partitioning tool 214 may partition the digitized pathology image into a second plurality of neighborhoods having a second size, etc.

In various embodiments, plurality of neighborhoods 216*a*-2126*n* may have sizes that are between approximately 100×100 image units (e.g., pixels, voxels, or the like) and approximately 1000×1000 image units. In some embodiments, the partitioning tool 214 may be configured to partition respective ones of the one or more digitized pathology images 104 into 9 different neighborhood sizes over 9 separate iterations. In some embodiments, the 9 different tumor neighborhood sizes may be 200×200 image units (e.g., pixels), 250×250 image units, 300×300 image units, 350×350 image units, 400×400 image units, 450×450 image units, 500×500 image units, 550×550 image units, and 600×600 image units.

The CFOD feature map generator 108 further comprises a CFOD measurement tool 217 that is configured to measure CFOD values within the plurality of neighborhoods 216*a*-216*n* associated with a particular neighborhood size. For example, during a first iteration the CFOD measurement tool 217 will measure CFOD values within a first plurality of neighborhoods having a first size (e.g., 200×200 image units), during a second iteration the CFOD measurement tool 217 will measure CFOD values within a second plurality of neighborhoods having a second size (e.g., 250×250 image units), etc. In some embodiments, the CFOD measurement tool 217 may measure CFOD values within the plurality of neighborhoods 216*a*-216*n* using a derivative-of-Gaussian based model to capture fiber orientations by identifying linear structures within stromal regions. To ensure that the detected linear structures do not overlap with segmented nuclei, a nuclei segmentation mask (e.g., a binary mask) may be used.

From the measured CFOD values, the CFOD feature map generator 108 is configured to generate one or more CFOD feature maps 110*a*-110*n*. The one or more CFOD feature maps 110*a*-110*n* respectively comprise CFOD values corresponding to the plurality of neighborhoods associated with a particular neighborhood size. For example, a first CFOD feature map 110*a* may comprise CFOD values for a first plurality of neighborhoods having a first size (e.g., 200×200), a second CFOD feature map 110*b* may comprise CFOD values for a second plurality of neighborhoods having a second size (e.g., 250×250), etc. In some embodiments, the CFOD feature map generator 108 may be configured to generate 9 different CFOD feature maps having CFOD values for neighborhoods with 9 different sizes.

In some embodiments, the CFOD feature map generator 108 may form the one or more CFOD feature maps 110*a*-110*n* by placing a CFOD value measured within a neighborhood into one of a plurality of discrete bins that respectively correspond to different CFOD values. For example, in some embodiments the measured CFOD values may be placed into one of eighteen discrete bins. In some such embodiments, for each tumor neighborhood, an orientation co-occurrence matrix may be constructed based on a set of fiber orientations. Each row and column in the orientation co-occurrence matrix corresponds to an angular bin, ranging from 0 to 17, obtained by discretizing collagen fiber orientations. The quantitative measurement of CFOD in the stromal regions may be subsequently computed from the orientation co-occurrence matrix using entropy theory, where entropy represents a level of uncertainty in the orientation of collagen fibers within a tumor neighborhood.

A CFOD feature generation component 114 is configured to operate upon the one or more CFOD feature maps 110*a*-110*n* to generate a plurality of CFOD features 118. In some embodiments, the CFOD feature generation component 114 may comprise a statistical analysis component 116 configured to operate upon the one or more CFOD feature maps 110*a*-110*n* to generate the plurality of CFOD features 118. In some embodiments, the plurality of CFOD features 118 may comprise first order statistics of the one or more CFOD feature maps 110*a*-110*n*. In some embodiments, the first order statistics may comprise a mean, a min, a max value, and/or the like.

The plurality of CFOD features 118 include measures of entropy associated with CFOD. For example, the plurality of CFOD features 118 may include a mean entropy value of a CFOD feature map, a minimum entropy value of a CFOD feature map, and a maximum entropy value of a CFOD feature map, and/or the like. In some embodiments, the plurality of CFOD features 118 include measures of entropy obtained using neighborhoods having different sizes. For example, the plurality of CFOD features 118 may include a mean entropy value of a CFOD feature map obtained using the first plurality of neighborhoods having a first size and a minimum entropy value of a CFOD feature map obtained using the second plurality of neighborhoods having a second size.

The plurality of CFOD features 118 are provided to a machine learning model 120 that is configured to utilize the plurality of CFOD features 118 to generate an EOC survival prognosis 122 for the patient 202. In some embodiments, the EOC survival prognosis 122 may comprise a risk of death (e.g., a 5-year overall survival). In some embodiment, the machine learning model 120 may comprise a neural network (e.g., a convolutional neural network) configured to implement a regression model (e.g., a Cox-proportional Hazards model).

Figures 3A, 3B, 3C:
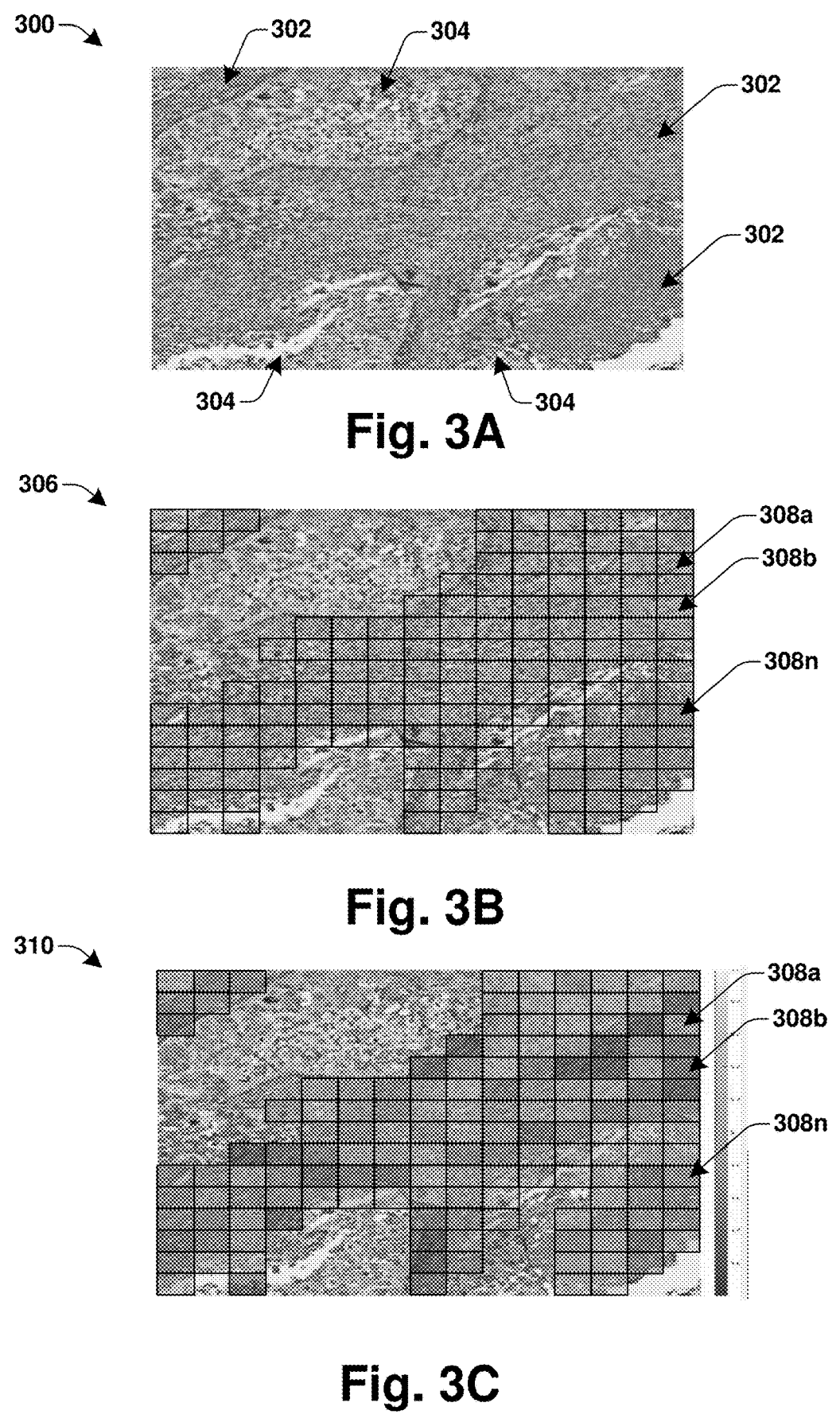

FIGS. 3A-3C illustrate some exemplary images corresponding to a measurement of CFOD within a whole slide image (WSI).

FIG. 3A illustrates a whole slide image 300 of a digitized H&E (Hematoxylin and Eosin) stained slide of epithelial tissue obtained during resection of an EOC tumor. The whole slide image 300 comprises one or more tumor regions 302 and one or more non-tumor regions 304. The one or more tumor regions 302 comprise tissue that is identified as being part of an EOC tumor. In some embodiments, the one or more tumor regions 302 and the one or more non-tumor regions 304 may be identified using a deep learning algorithm.

FIG. 3B illustrates a whole slide image 306 in which the one or more tumor regions (e.g., 302 of FIG. 3A) have been partitioned into a plurality of neighborhoods **308*a*-308*n*. The plurality of neighborhoods 308*a*-308*n* abut one another to cover the one or more tumor regions. In whole slide image 306, the plurality of neighborhoods 308*a*-308*n*** represent a tile size of 200×200 pixels. In other embodiments, other tile sizes may be used.

FIG. 3C illustrates a whole slide image 310 that has been overlaid with a CFOD feature map. The CFOD feature map shows that each of the plurality of neighborhoods **308*a*-308*n* has a CFOD value associated with it. The CFOD values have been discretized into bins, such that a CFOD value of a respective one of the plurality of neighborhoods 308*a*-308*n* is illustrated as having a color corresponding to a bin having a range of values. For example, a first color (e.g., yellow) corresponds to a first bin having a first range of CFOD values, a second color (e.g., blue) corresponds to a second bin having a second range of CFOD values, etc. The whole slide image 306 shown in FIG. 3C** has been discretized into 18 different bins (e.g., corresponding to 18 different colors). In other embodiments, a digitized pathology image may be discretized into other numbers of different bins (e.g., 5 bins, 8 bins, 9, bins, 20 bins, etc.).

FIG. 4 illustrates a table 400 showing some exemplary CFOD features that have been found to be determinative of an EOC survival prognosis (e.g., a risk of death, a 5-year overall survival, etc.) in a patient having or having had EOC. It has been appreciated that the features illustrated in table 400 are able to provide for good results in generating an EOC survival prognosis in a patient that has been treated for EOC by surgical resection and/or adjuvant chemotherapy. However, it will also be appreciated that the CFOD features shown in table 400 are only examples of CFOD features that may be used to generate an EOC survival prognosis and are not intended to limit the disclosure.

As shown in table 400, the CFOD features may comprise a mean entropy value of a CFOD feature map using a 200×200 pixel neighborhood, a minimum entropy value of a CFOD feature map using a 200×200 pixel neighborhood, a maximum entropy value of a CFOD feature map using a 250×250 pixel neighborhood, a minimum entropy value of a CFOD feature map using a 350×350 pixel neighborhood, a minimum entropy value of a CFOD feature map using a 400×400 pixel neighborhood, a minimum entropy value of a CFOD feature map using a 450×450 pixel neighborhood, a maximum entropy value of a CFOD feature map using a 550×550 pixel neighborhood, and a maximum entropy value of a CFOD feature map using a 600×600 pixel neighborhood.

Table 400 also illustrates a hazard ratio (HR) associated with each of the CFOD features. The HR indicates what type of correlation a CFOD feature has with a risk of an event (e.g., death). In other words, an HR value of greater than 1 means that an associated CFOD feature will be more prevalent in a high risk patient (e.g., a patient with low overall survival) than in a low risk patient (e.g., a patient with high overall survival), while an HR value of greater less 1 means that an associated CFOD feature will be less prevalent in a high risk patient (e.g., a patient with low overall survival) than in a low risk patient (e.g., a patient with high overall survival). For example, because a minimum entropy value of a CFOD feature map using a 450×450 pixel neighborhood has an HR value of 1.64, this CFOD feature will be more prevalent in a high risk patient and less prevalent in a low risk patient.

Figures 5A, 5B:
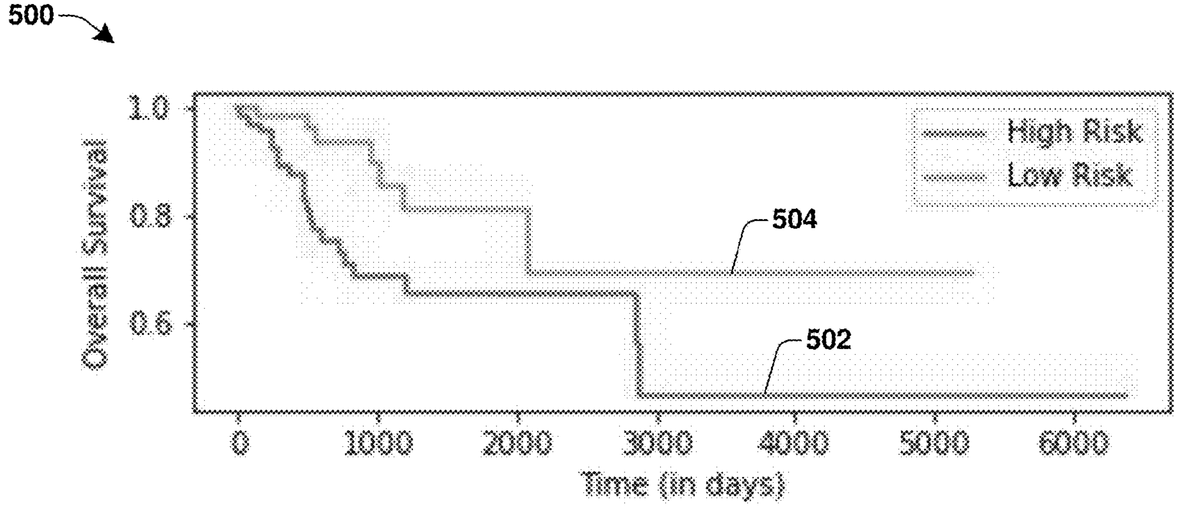
FIG. 5A illustrates a graph showing exemplary results of a disclosed EOC assessment system using univariant analysis.
FIG. 5B illustrates a chart showing exemplary results of a disclosed EOC assessment system using multivariable analysis controlling for prognostic clinical variables.

FIG. 5A illustrates a Kaplan Meier curve 500 showing exemplary results of a disclosed EOC assessment system using univariant analysis.

As shown in the Kaplan Meier curve 500, patients that were identified as being high risk patients 502 by a disclosed EOC assessment system are represented by a first trend line, while patients that were identified as being low risk patients 504 by a disclosed EOC assessment system are represented by a second trend line. The first trend indicates that high risk patients 502 have a lower overall survival time than the low risk patients 504, thereby confirming that the disclosed EOC assessment system is able to accurately predict overall survival of a patient. In some embodiments, a disclosed EOC assessment system is able to achieve a Hazard Ratio (HR)=2.55 for high-risk CFOD (95% Confidence Interval (CI)=1.15-5.7, p=0.02).

FIG. 5B illustrates a chart 506 showing exemplary results of a disclosed EOC assessment system using multivariable analysis controlling for prognostic clinical variables.

As shown in chart 506, the multivariable analysis controls for prognostic clinical variables including age, FIGO (Federation Internationale de Gynecologie et d'Obstetrique) stage, and CFOD. Chart 506 shows that FIGO stage (HR=2.3, CI=1.02-5.2, p=0.04) and CFOD (HR=2.47, CI=1.07-5.7, p=0.03) were independently associated with overall survival. The high HR of CFOD provides for a good indication that a disclosed EOC assessment system is able to accurately predict overall survival of a patient.

Figure 6:
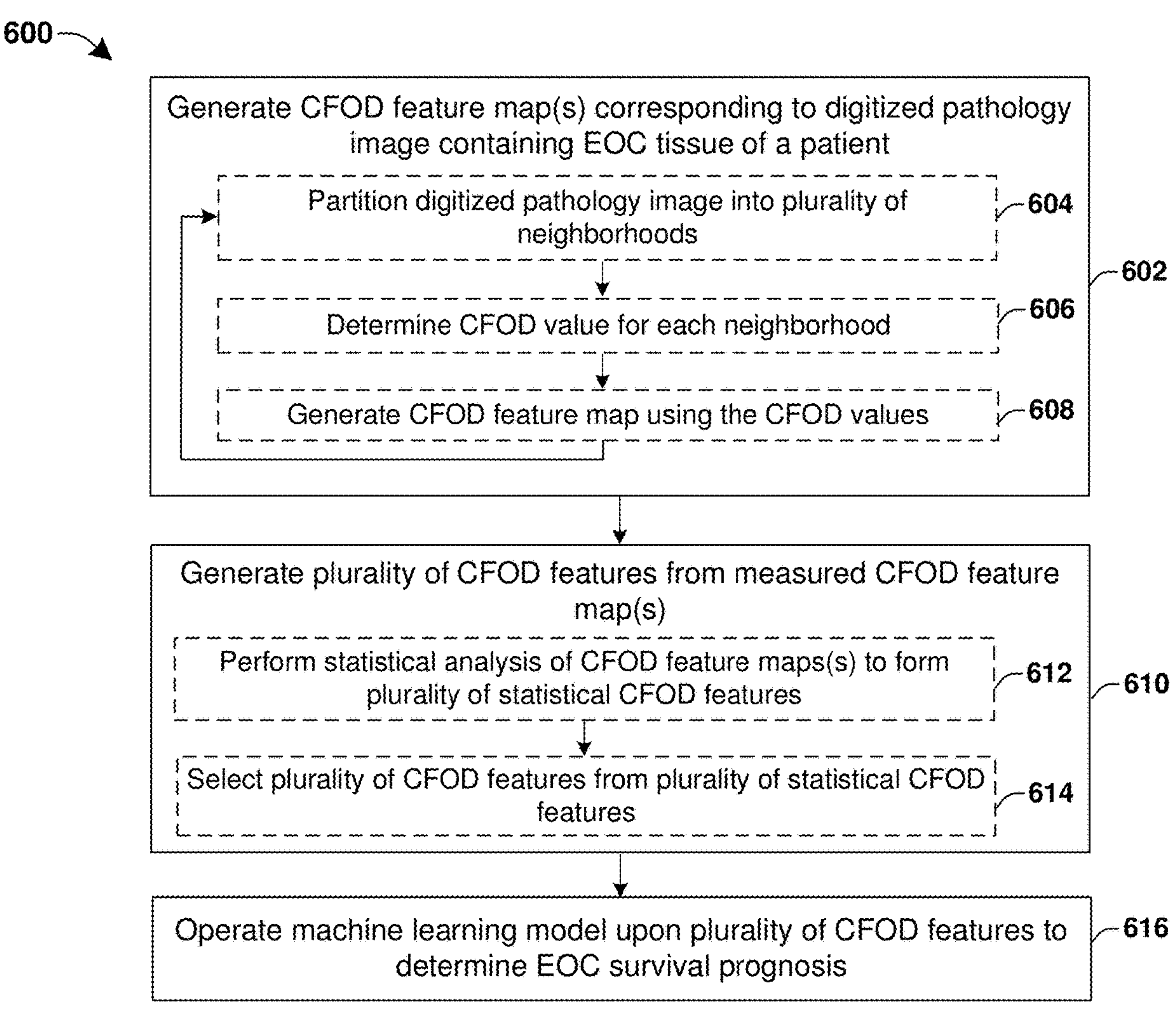
FIG. 6 illustrates a flow diagram of some embodiments of a method of determining a prognosis for a patient using CFOD features extracted from one or more digitized pathology images.

FIG. 6 illustrates a flow diagram of some embodiments of a method 600 of determining a prognosis for a patient using CFOD features extracted from one or more digitized pathology images of EOC tissue of the patient.

While the disclosed methods (e.g., methods 600 and 900) are illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At act 602, one or more CFOD feature maps are generated. The one or more CFOD feature maps correspond to a digitized pathology image containing EOC tissue of a patient. In some embodiments, the one or more CFOD feature maps may be generated according to acts 604-608.

At act 604, the digitized pathology image is partitioned into a plurality of neighborhoods.

At act 606, a CFOD value is determined for each of the plurality of neighborhoods.

At act 608, a CFOD feature map is generated using the CFOD values of the plurality of neighborhoods.

In some embodiments, acts 604-608 may be iteratively repeated for neighborhoods having different sizes to generate a plurality of CFOD feature maps corresponding to neighborhoods having the different sizes. For example, acts 604-608 may be performed a first time for neighborhoods having a first size to generate a first CFOD feature map, acts 604-608 may subsequently be performed a second time for neighborhoods having a second size to generate a second CFOD feature map, etc.

At act 610, a plurality of CFOD features are generated from the one or more CFOD feature maps. In some embodiments, the plurality of CFOD features may be generated according to acts 612-614.

At act 612, a plurality of statistical CFOD features are generated from the one or more CFOD feature maps by performing statistical analysis on the one or more CFOD feature maps. In some embodiments, the statistical analysis may comprise first order statistics (e.g., a mean, a max, and a min value) measured over a CFOD feature map.

At act 614, a plurality of CFOD features are selected from the plurality of statistical CFOD features.

At act 616, a machine learning model is operated upon plurality of CFOD features to determine an EOC survival prognosis (e.g., an overall survival, a risk of death, or the like).

It will be appreciated that the disclosed methods and/or block diagrams may be implemented as computer-executable instructions, in some embodiments. Thus, in one example, a computer-readable storage device (e.g., a non-transitory computer-readable medium) may store computer executable instructions that if executed by a machine (e.g., computer, processor) cause the machine to perform the disclosed methods and/or block diagrams. While executable instructions associated with the disclosed methods and/or block diagrams are described as being stored on a computer-readable storage device, it is to be appreciated that executable instructions associated with other example disclosed methods and/or block diagrams described or claimed herein may also be stored on a computer-readable storage device. In some embodiments, the computer-executable instructions may be implemented within a software package, so as to allow a health care professional to utilize the disclosed methods and/or block diagrams through the software package.

Figure 7:
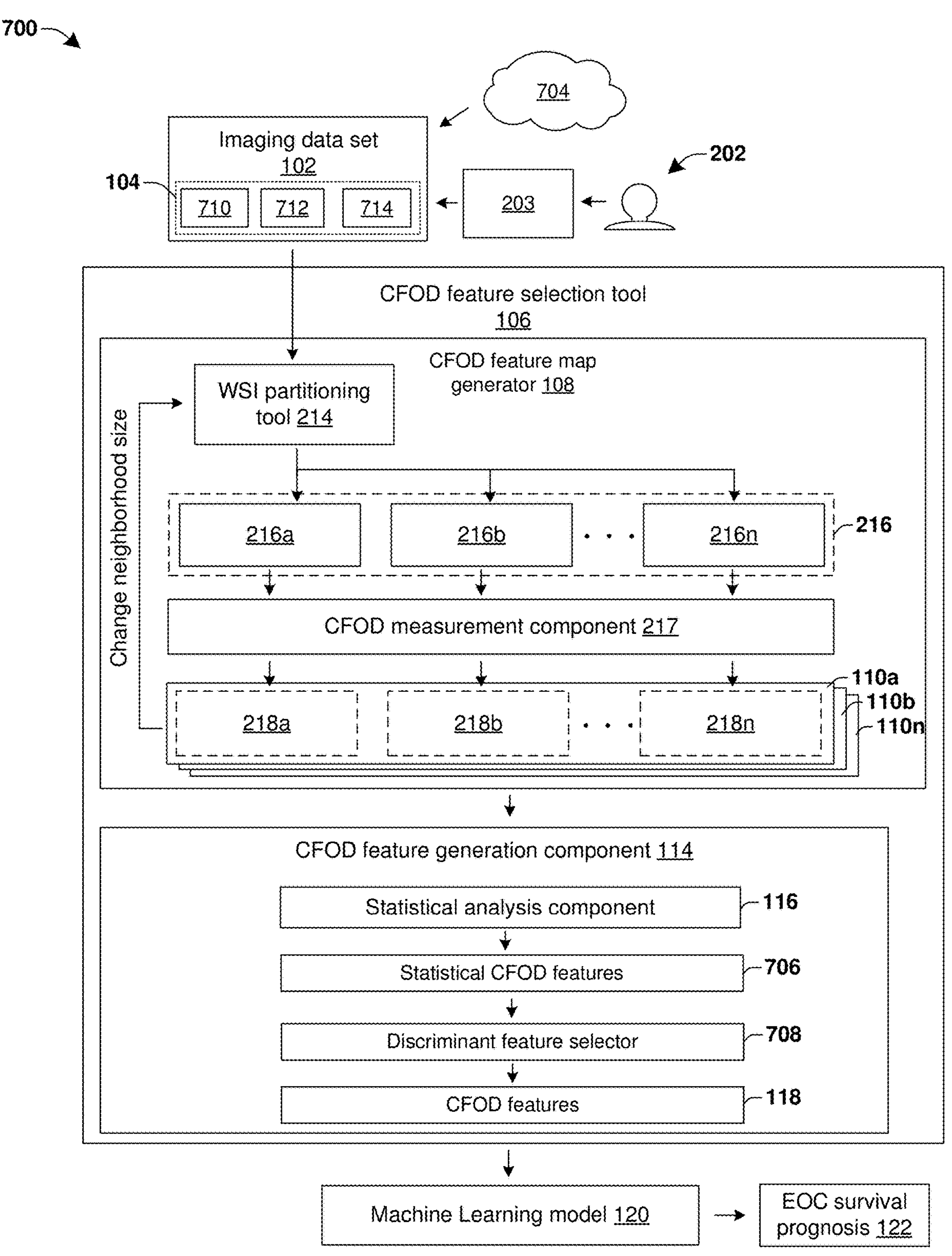
FIG. 7 illustrates a block diagram of some additional embodiments of an EOC assessment system that is configured to be trained to determine a prognosis for a patient using CFOD features extracted from one or more digitized pathology images.

FIG. 7 illustrates a block diagram of some additional embodiments of an EOC assessment system 700 that is configured to be trained to determine a prognosis for a patient using CFOD features extracted from one or more digitized pathology images of EOC tissue of the patient.

The EOC assessment system 700 comprises an imaging data set 102 including a plurality of digitized pathology images 104 obtained from a pathological tissue sample taken from the patient 202. The plurality of digitized pathology images 104 comprise WSIs of epithelial tissue including EOC (e.g., including an EOC tumor). In various embodiments, the plurality of digitized pathology images 104 may be obtained by a slide generation stage 203 and/or from an on-line database 704 and/or archive containing digitized pathology images from patients generated at different sites (e.g., different hospitals, research laboratories, and/or the like).

A CFOD features selection tool 106 is configured to access the plurality of digitized pathology images 104 and to extract a plurality of CFOD features 118 from the plurality of digitized pathology images 104. In some embodiments, the CFOD feature selection tool 106 may comprise a CFOD feature map generator 108 and a CFOD feature generation component 114.

The CFOD feature map generator 108 is configured to generate a plurality of CFOD feature maps 110*a*-110*n*. The plurality of CFOD feature maps 110*a*-110*n* respectively comprise a plurality of neighborhoods 218*a*-218*n* having an associated CFOD value. In some embodiments, respective ones of the plurality of neighborhoods 218*a*-218*n* may have a value that has been arranged in one of a plurality of discrete bins, so that the CFOD value is one of the plurality of discrete bins.

A CFOD feature generation component 114 is configured to operate upon the plurality of CFOD feature maps 110*a*-110*n* to generate a plurality of CFOD features 118. In some embodiments, the CFOD feature generation component 114 may comprise a statistical analysis component 116 configured to generate a plurality of statistical CFOD features 706 from the plurality of CFOD feature maps 110*a*-110*n*. A discriminant feature selector 708 is configured to operate upon the plurality of statistical CFOD features 706 to identify the plurality of CFOD features 118. In some embodiments, the plurality of CFOD features 118 are a subset of the plurality of statistical CFOD features 706, which are most determinative of overall survival within the patient 202 (e.g., that are mostly likely to lead to an accurate determination of overall survival). In some embodiments, the discriminant feature selector 708 may comprise a LASSO (least absolute shrinkage and selection operator) algorithm (e.g., a LASSO Cox regression model).

For example, in some embodiments the statistical analysis component 116 may be configured to generate a plurality of statistical CFOD features 706 comprising first-order statistics (e.g., a mean, a min, and a max value) of the one or more CFOD feature maps 110*a*-110*n* for 9 different neighborhood sizes to generate statistical CFOD features 706 that include a total of 27 statistical CFOD features. The discriminant features selector 708 is configured to operate upon the 27 statistical CFOD features 706 with a LASSO algorithm to identify the plurality of CFOD features 118 that include 8 CFOD features.

The plurality of CFOD features 118 are provided to a machine learning model 120 that is configured to generate an EOC survival prognosis 122. In some embodiments, the machine learning model 120 may comprise a neural network configured to implement a Cox proportional hazard model.

In some embodiments, the plurality of digitized pathology images 104 within the imaging data set 102 may comprise a training data set 710, a testing data set 712, and/or a validation data set 714. The training data set 710 may be used to train initial versions of the machine learning model. The initial versions of the machine learning model may be subsequently fine-tuned using the testing data set 712 to generate one or more evaluation models. The validation data set 714 may then be used to generate the machine learning model 120 from the one or more evaluation models.

In some embodiments, digitized pathology images may be subject to one or more inclusion and/or exclusion criteria to be included within the training data set 710, the testing data set 712, and/or the validation data set 714. Subjecting digitized pathology images to one or more inclusion and/or exclusion criteria provides for a better quality of data upon which to train the machine learning model 120, thereby providing for a more accurate trained machine learning model.

Figure 8:
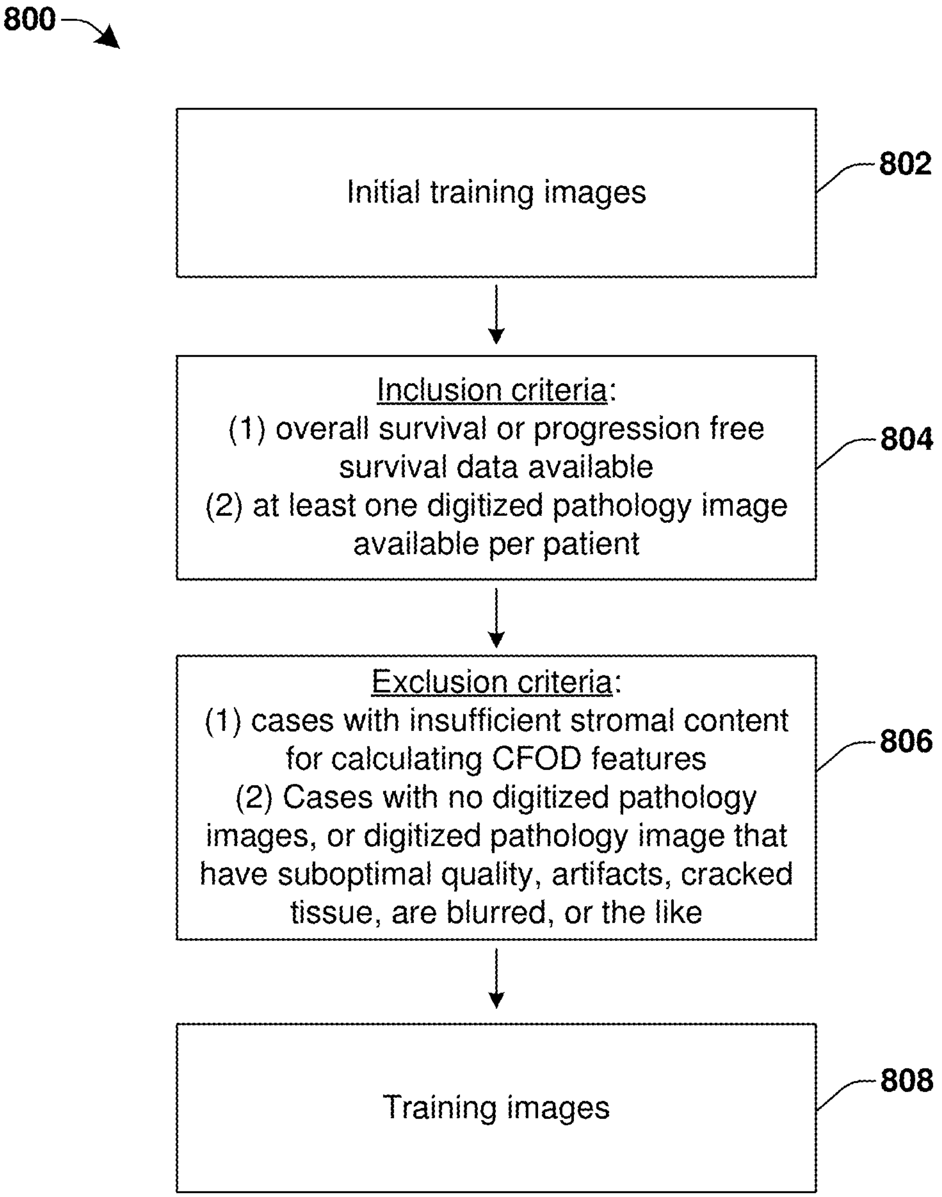
FIG. 8 illustrates a flow chart showing exemplary inclusion and exclusion criteria for training images used to train a disclosed EOC assessment system.

FIG. 8 illustrates a flow chart 800 showing exemplary inclusion and exclusion criteria for training a disclosed machine learning model (e.g., machine learning model 120 of FIG. 8) to determine an EOC survival prognosis for a patient using CFOD features extracted from one or more digitized pathology images of EOC tissue of the patient.

As shown in flow chart 800, initial training images 802 may comprise a first plurality of digitized pathology images. The initial training images 802 are filtered according to a set of inclusion criteria 804 and a set of exclusion criteria 806 to generate training images 808. In some embodiments, the inclusion criteria 804 may include images from patients for which overall survival or progression free survival data is available and at least one digitized pathology image is available. In some embodiments, the exclusion criteria 806 may exclude images from patients with insufficient stromal content for calculating CFOD features, and from patients that either have no digitized pathology images, have a blurred digitized pathology image, have a digitized pathology image with suboptimal quality, one or more artifacts, cracked tissue, and/or the like.

Images from the initial training images 802 that either fail to meet the set of inclusion criteria 804 or that meet the set of exclusion criteria 806 are discarded and do not become part of the training images 808. For example, an image associated with a patient that does not have overall survival or progression free survival data available will be discarded as it fails to meet one of the inclusion criteria 804.

Figure 9:
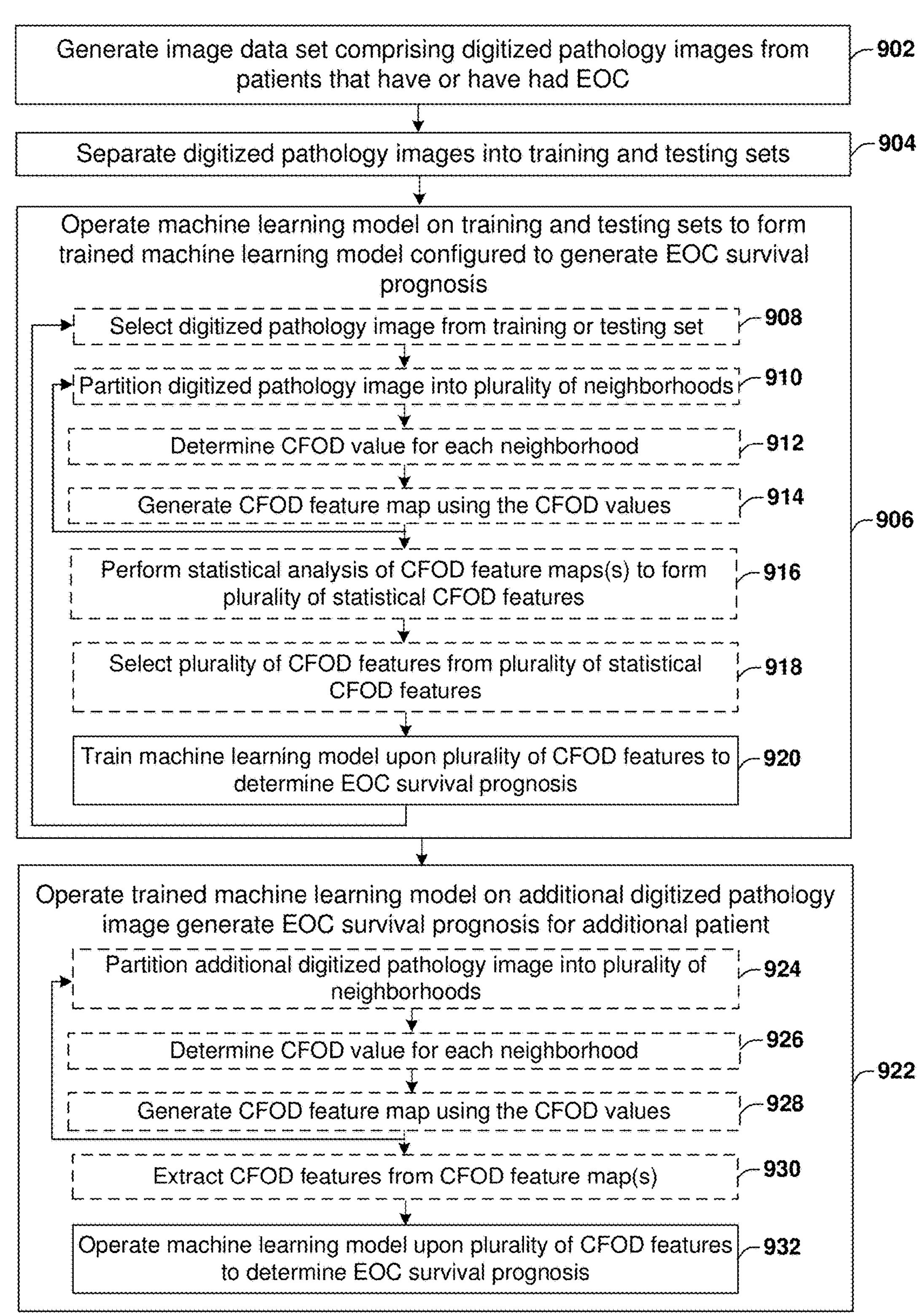
FIG. 9 illustrates a flow diagram of some embodiments of a method of training a disclosed EOC assessment system.

FIG. 9 illustrates a flow diagram of some embodiments of a method 900 of training a disclosed EOC assessment system.

At act 902, an imaging data set is formed to include a plurality of digitized pathology images of pathology slides from patients that have or that have had EOC.

At act 904, the plurality of digitized pathology images are separated into a training set and a testing set.

At act 906, a machine learning model is operated upon the training set and the testing set to generate a trained machine learning model configured to generate an EOC survival prognosis. In some embodiments, the machine learning model may be trained according to acts 908-920. It will be appreciated that the machine learning model may be trained by iteratively performing acts 908-920 on digitized pathology images within the training set and on digitized pathology images within the testing set. For example, acts 908-920 may be performed for a first number of n iterations on digitized pathology images within the training set. Subsequently, acts 908-920 may be performed for a second number of m iterations on digitized pathology images within the testing set.

At act 908, a digitized pathology image from the training set or the testing set is selected.

At act 910, the digitized pathology image is partitioned into a plurality of neighborhoods.

At act 912, CFOD values are determined for each of the plurality of neighborhoods.

At act 914, a CFOD feature map is generated using the CFOD values. In some embodiments, acts 910-912 may be iteratively performed on a same digitized image for different neighborhood sizes to form a plurality of CFOD feature maps.

At act 916, statistical analysis of the one or more CFOD features maps is performed to generate a plurality of statistical CFOD features.

At act 918, a plurality of CFOD features are selected from the plurality of statistical CFOD features.

At act 920, the machine learning model is trained on the plurality of CFOD features to determine an EOC survival prognosis.

At act 922, the trained machine learning model is operated upon an additional digitized pathology image to determine an EOC survival prognosis for an additional patient that has or that has had EOC. In some embodiments, the additional digitized pathology image may be obtained (e.g., by surgery) from the additional patient. In some embodiments, the trained machine learning model may be operated upon the additional digitized pathology image to determine the EOC survival prognosis for the additional patient according to acts 924-932.

At act 924, the additional digitized pathology image is partitioned into a plurality of neighborhoods.

At act 926, CFOD values are determined for each of the plurality of neighborhoods.

At act 928, a CFOD feature map is generated using the CFOD values. In some embodiments, acts 924-928 may be iteratively performed on a same digitized image for different neighborhood sizes to form a plurality of CFOD feature maps.

At act 930, the plurality of CFOD features are extracted from one or more CFOD feature maps.

At act 932, the machine learning model is operated upon the plurality of CFOD features to generate the EOC survival prognosis for the additional patient.

Figure 10:
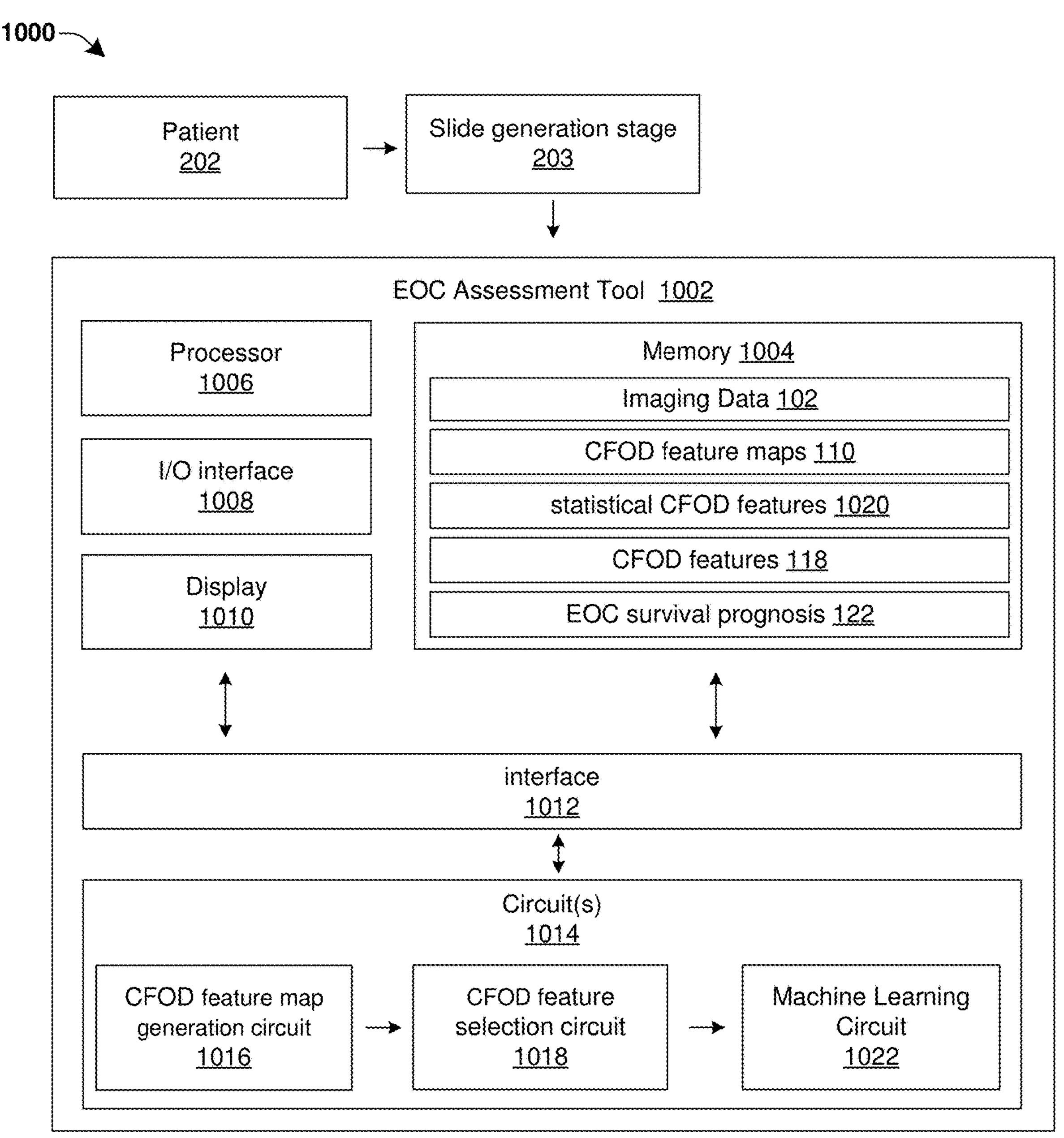
FIG. 10 illustrates a block diagram of some embodiments of a prognostic apparatus comprising a disclosed EOC assessment system.

FIG. 10 illustrates a block diagram of some embodiments of a prognostic apparatus 1000 comprising a disclosed EOC assessment tool.

The prognostic apparatus 1000 comprises an EOC assessment tool 1002. The EOC assessment tool 1002 is coupled to a slide generation stage 203 that is configured to generate one or more digitized pathology images (e.g., WSIs) of pathology slides corresponding to a patient 202.

The EOC assessment tool 1002 comprises a processor 1006 and a memory 1004. The processor 1006 can, in various embodiments, comprise circuitry such as, but not limited to, one or more single-core or multi-core processors. The processor 1006 can include any combination of general-purpose processors and dedicated processors (e.g., graphics processors, application processors, etc.). The processor 1006 can be coupled with and/or can comprise memory (e.g., memory 1004) or storage and can be configured to execute instructions stored in the memory 1004 or storage to enable various apparatus, applications, or operating systems to perform operations and/or methods discussed herein.

Memory 1004 can be further configured to store an imaging data set 102 comprising the one or more digitized pathology images (e.g., digitized WSIs) as a plurality of imaging units (e.g., pixels, voxels, etc.) respectively having an associated intensity. In some additional embodiments, the one or more digitized pathology images may be stored in the memory 1004 as one or more training sets of digitized pathology images for training a machine learning circuit and/or one or more testing sets of digitized pathology images.

The EOC assessment tool 1002 also comprises an input/output (I/O) interface 1008 (e.g., associated with one or more I/O devices), a display 1010, one or more circuits 1014, and an interface 1012 that connects the processor 1006, the memory 1004, the I/O interface 1008, the display 1010, and the one or more circuits 1014. The I/O interface 1008 can be configured to transfer data between the memory 1004, the processor 1006, the one or more circuits 1014, and external devices (e.g., slide generation stage 203).

In some embodiments, the one or more circuits 1014 may comprise hardware components. In other embodiments, the one or more circuits 1014 may comprise software components. In such embodiments, the one or more circuits 1014 may execute code stored in the memory 1004. The one or more circuits 1014 can comprise a CFOD feature map generation circuit 1016 configured to partition respective ones of the one or more digitized pathology images into a plurality of neighborhoods, to measure CFOD values within the plurality of neighborhoods, and to generate one or more CFOD feature maps 110 from the measured CFOD values within the plurality of neighborhoods.

In some additional embodiments, the one or more circuits 1014 may further comprise a CFOD feature selection circuit 1018. In some embodiments, the CFOD feature selection circuit 1018 is configured to operate upon the one or more CFOD feature maps 110 to generate a plurality of CFOD features 118. In some embodiments, the CFOD feature selection circuit 1018 may perform statistical analysis of the one or more CFOD feature maps 110 to generate a plurality of statistical CFOD features 1020, and subsequently select the plurality of CFOD features 118 from the plurality of statistical CFOD features 1020. In some embodiments, the one or more circuits 1014 may further comprise a machine learning circuit 1022 configured to utilize the plurality of CFOD features 118 to generate an EOC survival prognosis 122 for the patient.

Example Use Case 1:

Abstract

Background: Collagen fiber organization (CFO) may be associated with epithelial ovarian cancer (EOC) prognosis. EOC accounts for over 95% of ovarian malignancies, with five-year overall survival (OS)<50%. In this work, we use computational and machine learning tools to develop a quantitative biomarker of collagen fiber orientation disorder (CFOD) from H&E slides of EOC and evaluate its association with OS in women undergoing surgical resection followed by adjuvant chemotherapy.

Methods 1: Whole-Slide-Images of H&E slides from n=90 surgically resected EOC were obtained from TCGA, randomly split into training (St, n=50) and validation (Sv, n=40) sets. Each whole-slide-image was partitioned into an array of tumor neighborhoods. CFOD was calculated by quantifying entropy of fiber orientations in stromal regions within each neighborhood using a derivative-of-Gaussian model. The first-order-statistics of CFOD feature maps were extracted for 9 different neighborhood sizes. Among 72 extracted features, top 27 features selected by LASSO method were used to train Cox regression model assigning risk of death to each patient in St. The median CFOD-risk score was used to stratify patients as low or high-risk.

Methods 2: Data acquisition: Tumor resection, staining and formalin-fixing, paraffin-embedding and digitization. Finding features related to CFO: (1) Whole slide image partitioned into array of tumor neighborhoods (2) CFOD calculated by quantifying entropy of fiber orientations in stromal regions within each neighborhood using derivative-of-Gaussian model (3) First-order statistics of CFOD feature maps extracted for 9 different neighborhood sizes (4) 72 CFOD features, top 27 features selected by LASSO method. Feature selection and classification: Using LASSO Cox regression model for the experiments. Survival Analysis: (1) Univariate Analysis (2) Multivariable Analysis.

Results: In Sv, univariate analysis yielded Hazard Ratio (HR)=2.55 for high-risk CFOD (95% Confidence Interval (CI)=1.15-5.7, p=0.02). Multivariable analysis controlling for prognostic clinical variables (Age (<60), FIGO stage (II, III, IV)) showed FIGO stage (HR=2.3, CI=1.02-5.2, p=0.04) and CFOD (HR=2.47, CI=1.07-5.7, p=0.03) were independently associated with OS.

Interpretation: Our results found that CFO is more ordered in patients with worse OS. Independent multi-site validation could allow for deployment of CFOD as a prognostic decision support tool for management of EOC patients.

Therefore, the present disclosure relates to a method and associated apparatus for determining a prognosis for a patient having EOC using collagen fiber orientation disorder (CFOD) features extracted from digitized pathology images of EOC tissue excised from the patient. The disclosed method and associated apparatus are able to achieve an improved performance over traditional manual assessments because the CFOD features that the disclosed method and apparatus extracts from the digitized pathology images are at a higher order or higher level than a human can resolve in the human mind or with pencil and paper. For example, the CFOD features measure entropy in a manner that cannot be identified by a human.

In some embodiments, the present disclosure relates to a method for determining a prognosis. The method includes measuring a collagen fiber orientation disorder (CFOD) within a digitized pathology image of epithelial tissue removed from a patient that has or that has had epithelial ovarian cancer (EOC); generating a plurality of CFOD features using the measured CFOD; and operating a machine learning model upon the plurality of CFOD features to determine an EOC survival prognosis for the patient.

In other embodiments, the present disclosure relates to a non-transitory computer-readable medium storing computer-executable instructions that, when executed, cause a processor to perform operations, including partitioning a whole slide image corresponding to a patient having or having had epithelial ovarian cancer (EOC) into a plurality of neighborhoods having a first size; determining a CFOD value for each of the plurality of neighborhoods; generating a CFOD feature map using the CFOD value for each of the plurality of neighborhoods; performing a statistical analysis of the CFOD feature map to form a plurality of statistical CFOD features; selecting a plurality of CFOD features from the plurality of statistical CFOD features; and operating a machine learning model upon the plurality of CFOD features to determine an EOC survival prognosis for the patient.

In yet other embodiments, the present disclosure relates to an apparatus. The apparatus includes a partitioning tool configured to partition a digitized pathology image into a plurality of neighborhoods having a first size, wherein the digitized pathology image is from a patient having or having had epithelial ovarian cancer (EOC); a CFOD feature map generator configured to determine a CFOD value for each of the plurality of neighborhoods and to generate a CFOD feature map using the CFOD value for each of the plurality of neighborhoods; a CFOD feature generation component configured to perform a statistical analysis of the CFOD feature map to form a plurality of statistical CFOD features and to select a plurality of CFOD features from the plurality of statistical CFOD features; and a machine learning model configured to operate upon the plurality of CFOD features to determine an EOC prognosis for the patient.

Examples herein can include subject matter such as an apparatus, a digital whole slide scanner, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method for determining a prognosis, comprising:

partitioning a digitized pathology image of epithelial tissue removed from a patient that has or that has had epithelial ovarian cancer (EOC) into a plurality of spatially distinct neighborhoods;

measuring collagen fiber orientation disorder (CFOD) values for respective ones of the plurality of spatially distinct neighborhoods;

generating one or more CFOD feature maps comprising distinct regions that respectively include the CFOD values corresponding to one of the plurality of spatially distinct neighborhoods;

generating a plurality of CFOD features using the one or more CFOD feature maps, wherein the plurality of CFOD features comprise measures of entropy associated with CFOD; and operating a machine learning model upon the plurality of CFOD features to determine an EOC survival prognosis for the patient.

2. The method of claim 1, further comprising:

performing statistical analysis of the one or more CFOD feature maps to form a plurality of statistical CFOD features; and selecting one or more of the plurality of statistical CFOD features as the plurality of CFOD features.

3. The method of claim 1, further comprising:

measuring the CFOD value within the respective ones of the plurality of spatially distinct neighborhoods by using a derivative-of-Gaussian based model to capture fiber orientations by identifying linear structures within stromal regions within the respective ones of the plurality of spatially distinct neighborhoods.

4. The method of claim 1, wherein the digitized pathology image is a whole slide image (WSI) of a digitized H&E (Hematoxylin and Eosin) stained slide.

5. The method of claim 1, wherein the EOC survival prognosis is a 5-year overall survival of the patient after undergoing surgical resection and adjuvant chemotherapy.

6. The method of claim 1, wherein the plurality of CFOD features include one or more of a mean entropy value of a CFOD feature map using a 200×200 pixel neighborhood, a minimum entropy value of a CFOD feature map using a 200×200 pixel neighborhood, a maximum entropy value of a CFOD feature map using a 250×250 pixel neighborhood, a minimum entropy value of a CFOD feature map using a 350×350 pixel neighborhood, a minimum entropy value of a CFOD feature map using a 400×400 pixel neighborhood, a minimum entropy value of a CFOD feature map using a 450×450 pixel neighborhood, a maximum entropy value of a CFOD feature map using a 550×550 pixel neighborhood, and a maximum entropy value of a CFOD feature map using a 600×600 pixel neighborhood.

7. The method of claim 1, comprising:

partitioning the digitized pathology image into a first plurality of neighborhoods respectively having a first size;

determining a first plurality of CFOD values respectively corresponding to the first plurality of neighborhoods;

generating a first CFOD feature map using the first plurality of CFOD values;

partitioning the digitized pathology image into a second plurality of neighborhoods respectively having a second size, the second size being different than the first size;

determining a second plurality of CFOD values respectively corresponding to the second plurality of neighborhoods; and generating a second CFOD feature map using the second plurality of CFOD values.

8. The method of claim 1, wherein the machine learning model is configured to determine an overall survival of the patient as being inversely proportional to the measures of entropy associated with CFOD.

9. A non-transitory computer-readable medium storing computer-executable instructions that, when executed, cause a processor to perform operations, comprising:

partitioning a whole slide image corresponding to a patient having or having had epithelial ovarian cancer (EOC) into a plurality of neighborhoods having a plurality of different sizes;

determining a CFOD value for each of the plurality of neighborhoods;

generating a plurality of CFOD feature maps using the CFOD value for each of the plurality of neighborhoods;

performing a statistical analysis of the plurality of CFOD feature maps to form a plurality of statistical CFOD features;

selecting a plurality of CFOD features from the plurality of statistical CFOD features; and operating a machine learning model upon the plurality of CFOD features to determine an EOC survival prognosis for the patient.

10. The non-transitory computer-readable medium of claim 9, wherein the plurality of CFOD features include one or more of a mean entropy value of a CFOD feature map, a minimum entropy value of a CFOD feature map, and a maximum entropy value of a CFOD feature map.

11. The non-transitory computer-readable medium of claim 9, wherein each of the plurality of CFOD feature maps corresponds to a group of the plurality of neighborhoods having a same size of the plurality of different sizes.

12. A prognostic apparatus, comprising:

a partitioning tool configured to partition a digitized pathology image in an iterative process, wherein during the iterative process the digitized pathology image is partitioned into a plurality of neighborhoods having different sizes during different iterations, and wherein the digitized pathology image is from a patient having or having had epithelial ovarian cancer (EOC);

a CFOD feature map generator configured to determine a CFOD value for each of the plurality of neighborhoods and to generate a CFOD feature map using the CFOD value for each of the plurality of neighborhoods;

a CFOD feature generation component configured to perform a statistical analysis of the CFOD feature map to form a plurality of statistical CFOD features and to select a plurality of CFOD features from the plurality of statistical CFOD features; and a machine learning model configured to operate upon the plurality of CFOD features to determine an EOC prognosis for the patient.

13. The prognostic apparatus of claim 12, wherein the plurality of CFOD features include measures of entropy obtained using the plurality of neighborhoods.

14. The prognostic apparatus of claim 12, wherein the plurality of CFOD features include a mean entropy value of a CFOD feature map, a minimum entropy value of a CFOD feature map, and a maximum entropy value of a CFOD feature map.

15. The prognostic apparatus of claim 12, wherein the machine learning model is configured to determine an overall survival of the patient as being inversely proportional to a CFOD with in the patient.

16. The method of claim 1, wherein measuring CFOD values for the plurality of spatially distinct neighborhoods comprises:

constructing an orientation co-occurrence matrix for the plurality of spatially distinct neighborhoods based on a set of discrete fiber orientations, wherein each row and column in the orientation co-occurrence matrix corresponds to an angular bin; and computing a quantitative measurement of CFOD from the orientation co-occurrence matrix using entropy theory.

17. The method of claim 1, further comprising performing a statistical analysis of the one or more CFOD feature maps to form a plurality of statistical CFOD features, wherein the plurality of CFOD features is a subset of the plurality of statistical CFOD features.

18. The non-transitory computer-readable medium of claim 9, further comprising:

partitioning the whole slide image into a first plurality of neighborhoods respectively having a first size;

determining first CFOD values for the first plurality of neighborhoods;

generating a first CFOD feature map using the first CFOD values;

partitioning the whole slide image into a second plurality of neighborhoods respectively having a second size that is different than the first size;

determining second CFOD values for the second plurality of neighborhoods;

generating a second CFOD feature map using the second CFOD values; and performing the statistical analysis of the first CFOD feature map and the second CFOD feature map to form the plurality of statistical CFOD features.

19. The non-transitory computer-readable medium of claim 9, wherein partitioning the whole slide image into the plurality of neighborhoods comprises an iterative process, wherein a first iteration partitions the whole slide image into a first plurality of neighborhoods having a first size, and a second iteration partitions the whole slide image into a second plurality of neighborhoods having a second size.

20. The non-transitory computer-readable medium of claim 19, wherein determining the CFOD value for each of the plurality of neighborhoods comprises measuring the CFOD value for each of the first plurality of neighborhoods during the first iteration, and measuring the CFOD value for each of the second plurality of neighborhoods during the second iteration.

* * * * *